United States Patent [19]
Gould

[11] Patent Number: 4,847,277
[45] Date of Patent: Jul. 11, 1989

[54] COMPOUND AND TREATMENT OF OBSTRUCTIVE AIRWAYS DISEASE THEREWITH

[75] Inventor: Kenneth J. Gould, Long Whatton, England

[73] Assignee: Fisons plc, Ipswich, England

[21] Appl. No.: 204,079

[22] Filed: Jun. 8, 1988

[30] Foreign Application Priority Data

Jun. 24, 1987 [GB] United Kingdom ............... 8714839

[51] Int. Cl.$^4$ .................. C07D 257/04; A61K 31/41
[52] U.S. Cl. ..................................... 514/382; 548/253
[58] Field of Search .......................... 514/382; 548/253

Primary Examiner—David B. Springer
Attorney, Agent, or Firm—Marshall, O'Toole, Gerstein, Murray & Bicknell

[57] ABSTRACT

There is described the calcium salt of 10-propyl-2,8-bis(1H-tetrazol-5-yl)-4H,6H-benzo(1,2-b;5,4-b')dipyran-4,6- dione and processes for its preparation.

Also described are pharmaceutical compositions containing the calcium salt and methods of treatment involving its use.

9 Claims, No Drawings

COMPOUND AND TREATMENT OF OBSTRUCTIVE AIRWAYS DISEASE THEREWITH

This invention relates to a new compound, methods for its preparation and compositions containing it.

Disodium 10-propyl-2,8-bis(1H-tetrazol-5-yl)-4H,6H-benzo(1,2-b;5,4-b')dipyran-4,6-dione is disclosed in European Patent Specification No. 0150966 and has been shown to be of potential utility inter alia in the treatment of reversible obstructive airways disease. However, whilst the duration of action of this sodium salt is considerable, it is sometimes insufficient to enable a patient to obtain a full night's sleep. Furthermore, some patients experience side effects with the sodium salt.

Surprisingly, we have now found that calcium 10-propyl-2,8-bis(1H-tetrazol-5-yl)-4H,6H-benzo (1,2-b;5,4-b')dipyran-4,6-dione possesses advantageous properties in that it is more effective, suffers less from loss of responsiveness, produces fewer side effects, can be used at lower doses, can be administered less frequently, is longer acting, is more stable, causes better patient compliance, has a less offensive taste or possesses other desirable properties as compared with known compounds, e.g. the corresponding disodium salt, when tested in relevant pharmacological models.

Thus, according to the invention we provide calcium 10-propyl-2,8-bis(1H-tetrazol-5-yl)-4H,6H-benzo (1,2-b;5,4-b')dipyran-4,6-dione, hereinafter referred to as "the Compound".

We further provide a process for the manufacture of the Compound, which process comprises:

(a) reacting a solution of a suitable salt of 10-propyl-2,8bis (1H-tetrazol-5-yl)-4H,6H-benzo(1,2-b;5,4-b') dipyran-4,6-dione with an appropriate solution containing calcium cations in available form, or (b) reacting the free tetrazole, 10-propyl-2,8-bis (1H-tetrazol-5-yl) -4H,6H-benzo(1,2b;5,4-b')dipyran-4,6-dione, with a base containing the calcium cation in available form.

In the reaction of process (a), the salt used as a starting material may be formed in situ, and need not be isolated before use in a metathetical process. Suitable salts for use as a starting material include any salts which are soluble in the solvent used, for example the alkali metal salts, e.g. the disodium salt.

The reactions of processes (a) and (b) may be carried out in a solvent which is inert under the reaction conditions. The solvent is preferably one in which the Compound is relatively insoluble, e.g. acetone or water. The temperature at which the reaction is performed may be varied, but is preferably between 0° and 50° C., e.g. room temperature.

The calcium cations may be provided by any conventional form of calcium which has an appropriate solubility for dissolution in the solvent of choice, e.g. when the solvent is water, calcium nitrate or calcium chloride.

Preparation of 10-propyl-2,8-bis(IH-tetrazol-5-yl)-4H,6H-benzo(1,2-b;5,4-b')dipyran-4,6-dione and the disodium salt thereof is described in European Patent Application No. 0150966.

The Compound is useful because it possesses pharmacological activity in animals; in particular, it is useful because it inhibits the release and/or action of pharmacological mediators which result from the in vivo combination of certain types of antibody and specific antigen, e.g. the combination of reaginic antibody with specific antigen (see Example 27 of British Patent Specification No. 1,292,601). The Compound has also been found to interfere with reflex pathways in experimental animals and man, and in particular those reflexes associated with lung function. In man, both subjective and objective changes which result from the inhalation of specific antigen by sensitised subjects are inhibited by prior administration of the Compound. Thus, the Compound is indicated for use in the treatment of the conditions known generically as "reversible obstructive airways disease". Such conditions include allergic asthma, so-called 'intrinsic' asthma (in which no sensitivity to extrinsic antigen can be demonstrated), bronchitis and the nasal and bronchial obstructions associated with the common cold.

The Compound may also be of value in the treatment of other conditions in which antigen-antibody reactions or excess mucous secretion are responsible for, or are an adjunct to, disease, for example, coughs; seasonal rhinitis, e.g. hay fever; perennial rhinitis; nasal polyps; allergic manifestations of the nasopharynx; certain eye conditions, e.g. trachoma; alimentary allergy, e.g. urticaria and atopic eczema; and gastro-intestinal conditions, for example, gastro-intestinal allergy, especially in children, e.g. milk allergy, or ulcerative colitis.

Thus, according to a further aspect of the invention, there is provided a method of treatment of reversible obstructive airways disease which comprises administration of a therapeutically useful amount of the Compound to a patient suffering from or susceptible to such a condition.

In another aspect of the invention, there is provided the use of the Compound in the manufacture of a medicament for the treatment or prevention of reversible obstructive airways disease.

For the above-mentioned uses, the dosage administered will, of course, vary with the mode of administration and the treatment desired. However, in general, satisfactory results are obtained when the compound is administered at a dosage of from 0.001 to 50 mg per kg of animal body weight in the test set out in Example 27 of British Patent Specification No. 1,292,601. For man, the indicated total daily dosage is in the range of from 0.01 to 1000 mg, preferably from 0.01 to 600 mg, and more preferably from 1 to 200 mg, and may be administered in divided doses from 1 to 8 times a day or in sustained released form.

The Compound will generally be administered as a composition including one or more additional pharmaceutically acceptable additives. Thus, according to another aspect of the invention there is provided a pharmaceutical composition comprising less than 80%, more preferably less than 50% w/w, of the Compound in admixture with a pharmaceutically acceptable carrier.

The Compound may be administered by a variety of routes, e.g. orally, rectally or topically. Topical administration includes administration to the skin, by oral inhalation, to the nose or to the eye. We prefer the Compound to be administered topically to the nose, to the eye or, especially, by oral inhalation to the lung.

For administration to the lung, the Compound may be formulated as an aqueous solution or, more preferably, as a powder. Powder formulations may be non-pressurised or, more preferably, pressurised.

Thus, according to a preferred aspect of the invention, there is provided a pharmaceutical composition comprising the Compound in finely divided form in admixture with a pressurised pharmaceutically acceptable propellant.

In the pressurised powder composition, the propellant, and indeed the total composition, is preferably such that the Compound does not dissolve therein to any substantial extent.

The pressurised powder composition preferably contains less than 5%, more preferably less than 2.5%, and especially less than 1.5% w/w of the Compound.

The propellant is preferably a gas at room temperature (20° C.) and atmospheric pressure, i.e. it should have a boiling point below 20° C. at atmospheric pressure. The propellant should also be non-toxic. Among the suitable propellants which may be employed are dimethyl ether and alkanes containing up to five carbon atoms, e.g. butane or pentane, or a lower alkyl chloride, e.g. methyl, ethyl or propyl chlorides. The most suitable liquefied propellants are the fluorinated and fluorochlorinated lower alkanes such as are sold under the Registered Trade Mark 'Freon'. Mixtures of the above mentioned propellants may suitably be employed.

The pressurised composition may also contain a surface active agent. The surface active agent may be a liquid or solid non-ionic surface active agent or may be a solid anionic surface active agent.

The preferred solid anionic surface active agents are the docusate salts, e.g. calcium docusate or sodium docusate.

The amount of the surface active agent required may be related to the solids content of the suspension and to the particle size of the solids.

When a liquid, non-ionic surface-active agent is employed it may have a hydrophile-lipophile balance (HLB) ratio of less than 10. It is possible to employ mixtures of surface-active agents, the mixture having an HLB ratio within the prescribed range.

Those surface-active agents which are soluble or dispersible in the propellant are effective. The more propellant-soluble surface-active agents are the most effective.

Any conventional liquid non-ionic surface-active agents may be employed, e.g. the esters or partial esters of fatty acids containing from 6 to 22 carbon atoms.

We particularly prefer compositions containing a sorbitan or sorbitol ester, e.g. sorbitan trioleate, in a mixture of propellants.

We prefer packages containing from about 8 to 30ml of pressurised powder composition, e.g. a conventional aerosol pressure pack of 10ml. The pack preferably has a valve adapted to deliver unit dosages of between 0.025 and 0.25 ml, and preferably 0.05 or 0.1 ml, of composition. We prefer the valve to deliver 0.1 to 5 mg of Compound per actuation, preferably 0.1 to 4 mg, and more preferably 0.5 to 2 mg per actuation, and unit doses of these quantities of the Compound are another feature of the invention.

The pressurised composition may be made by mixing the various components at a temperature and pressure at which the propellant is in the liquid phase and the Compound is in the solid phase.

In producing packages of the pressurised powder compositions, a container equipped with a valve may be filled with a propellant containing the finely-divided Compound in suspension. The container may first be charged with a weighed amount of dry Compound which has been ground to a predetermined particle size, or with a slurry of powder in the cooled liquid propellant. The container may also be filled by introducing powder and propellant by the normal cold filling method, or a slurry of the powder in a component of the propellant which boils above room temperature may be placed in the container, the valve sealed in place, and the balance of the propellant may be introduced by pressure filling through the valve nozzle. As a further alternative a bulk quantity of the total composition may be made and portions of this bulk composition may be filled into the container through the valve. Throughout the preparation of the package care is desirably exercised to minimise the absorption of moisture. On operating the valve, the powder will be dispensed in a stream of propellant, which will vaporise providing an aerosol of powder.

For inhalation as a non-pressurised powder formulation, the Compound in finely divided form may be used in admixture with a carrier of larger particle size.

The particle size spectrum of the carrier will depend on the particular inhalation device from which the formulation is to be dispensed. It is however desirable to avoid carrier particles of less than 10 microns in size, thus minimising the number of non-drug particles which penetrate deep into the lung. A large proportion of very large particles may also cause a gritty feel in the mouth of the user and is therefore less preferred. Use of a carrier of larger particle size may also cause problems in filling when using filling machines which involve a dosator which picks up powder by dipping into a powder bed from above. However, use of a carrier of larger particle size may facilitate filling when using machines in which a die is filled from above, but may cause the composition to separate during transport or storage.

The non-pressurised formulation preferably contains from 2 to 50% w/w of the Compound, and from 50 to 98% w/w, more preferably from 75 to 95% w/w and particularly from 85 to 90% w/w of the carrier.

The carrier may be prepared by spray drying or grinding and subsequently separating out the desired fraction, for example by air classification and/or sieving.

The non-pressurised powder formulation may be prepared by mixing the ingredients together in one or, preferably, more (e.g. two) steps in a mixer, such as a planetary or other stirred mixer.

The carrier may be any non-toxic material which is chemically inert to the Compound and is acceptable for inhalation or for administration to the nose. Examples of carriers which may be used include inorganic salts, e.g. sodium chloride or calcium carbonate; organic salts, e.g. sodium tartrate or calcium lactate; organic compounds, e.g. urea or propylidone; monosaccharides, e.g. lactose, mannitol, arabinose or dextrose monohydrate; disaccharides, e.g. maltose or sucrose, polysaccharides, e.g. starches, dextrins or dextrans. A particularly preferred carrier is lactose, e.g. crystalline lactose.

Non-pressurised powder formulations will generally be put up in sealed gelatine, plastic or other capsules. The container is preferably loosely filled to less than about 80% by volume, preferably less than about 50% by volume, with the powder composition.

For use in pressurised or non-pressurised powder formulations, the finely divided Compound may be prepared in the desired particle size range, for example using a ball mill, a fluid energy mill, by precipitation or by spray drying. The water content of the Compound when used in such formulations is preferably less than 15%, more preferably from about 6 to 12%, e.g. about 10% w/w.

The invention is illustrated, but in no way limited, by the following Examples.

EXAMPLE 1

Preparation of the Compound

Disodium 10-propyl-2,8-bis(IH-tetrazol-5-yl)-4H,6H-benzo (1,2-b:5,4-b')dipyran-4,6-dione (988 g) was dissolved in deionised water (approximately 11 litres) and filtered into a fibre-free flask fitted with an efficient stirrer. Calcium chloride hexahydrate (836 g) was dissolved in deionised water (approximately 2.6 litres) and the solution was added rapidly to the solution of the sodium salt. After approximately 1 minute, the Compound began to precipitate out. The mixture was stirred overnight.

The product was slowly filtered off, rinsed with fibre-free water, sucked dry (48 hours) and dried in a vacuum oven at 75° C. for 30 hours.

Yield: 913 g (94%) 8.5% moisture.

EXAMPLE 2

Administration of the Compound by Pressurised Aerosol

Doses of the Compound (0.5 to 8 mg) were administered to 20 healthy human volunteers by oral administration to the lung using a pressurised aerosol.

Aqueous solutions of the corresponding sodium salt (0.5 to 20 mg/ml) were administered for comparison.

The incidence of the feeling of warmth as a side effect was markedly reduced with the Compound in comparison with the sodium salt.

EXAMPLE 3

Measurement of Anti-Allergic Activity

The activity of the Compound can be evaluated using an antigen inhalation test on human volunteers. The degree of asthma provoked by the inhalation of an antigen to which the volunteers are sensitive can be determined by repeated measurement of the increase in airway resistance as follows:

A suitably designed spirometer is used to measure the forced expiratory volume at one second ($FEV_1$) before and after antigen challenge. The anti-allergic activity of the Compound is expressed in terms of:

$$\% \text{ Protection} = 100 \times \frac{\Delta FEV_1(\text{control}) - \Delta FEV_1(\text{test})}{\Delta FEV_1(\text{control})}$$

where $\Delta FEV_1(\text{control})$=fall in FEVhd 1 following antigen challenge with no prior administration of Compound. and $\Delta FEV_1(\text{test})$=fall in $FEV_1$ following antigen challenge after prior administration of Compound.

EXAMPLE 4

Pressurised Aerosol Formulations for oral inhalation (a) Packages delivering 0.5 mg per actuation

| Material | Percent by weight | | |
|---|---|---|---|
| | A | B | C |
| Compound | 0.72 | 0.72 | 0.72 |
| Sorbitan trioleate | 0.25 | 0.50 | 1.00 |
| Propellant 114 | 39.61 | 39.51 | 39.31 |
| Propellant 12 | 59.42 | 59.27 | 58.97 |

Preparation method

Disperse the sorbitan trioleate in the propellant 12, cooled to −60° C. Add the micronised Compound and disperse thoroughly. Add the propellant 114, cooled to −60° C., mix and fill into aerosol cans. Crimp on a 50 microlitre metering valve.

(b) Package delivering 0.1 mg per actuation

| Material | Percent by weight | | |
|---|---|---|---|
| | A | B | C |
| Compound | 1.44 | 1.44 | 1.44 |
| Sorbitan trioleate | 0.25 | 0.50 | 1.00 |
| Propellant 114 | 39.32 | 39.22 | 39.02 |
| Propellant 12 | 58.99 | 58.84 | 58.54 |

Prepared by the method of Example 4(a).

(c) Packages delivering 2.0 mg per actuation

| Material | Percent by weight | | |
|---|---|---|---|
| | A | B | C |
| Compound | 1.44 | 1.44 | 1.44 |
| Sorbitan trioleate | 0.25 | 0.50 | 1.00 |
| Propellant 114 | 39.32 | 39.22 | 39.02 |
| Propellant 12 | 58.99 | 58.84 | 58.54 |

Prepared by the method of Example 4(a) using 100 microliter metering valves.

I claim:

1. Calcium 10-propyl-2,8-bis(1H-tetrazol-5yl)-4H,6H-benzo(1,2-b;5,4-b')dipyran-4,6-dione.

2. A pharmaceutical composition comprising less than 50% w/w of the compound of claim 1 as active ingredient in admixture with a pharmaceutically acceptable carrier.

3. A pharmaceutical composition according to claim 2, wherein the active ingredient is in powder form.

4. A pharmaceutical composition according to claim 2, which comprises the active ingredient in powder form and a pharmaceutically acceptable pressurized propellant.

5. A pharmaceutical composition according to claim 4, which includes a surfactant.

6. A pharmaceutical composition according to claim 4, which comprises less than 5% w/w of the active ingredient.

7. A pharmaceutical composition according to claim 2, which is non-pressurized and comprises between 2 and 50% w/w of the active ingredient in powder form.

8. A pharmaceutical composition according to claim 3, wherein the water content of the active ingredient is between 6 and 12% w/w.

9. A method of treatment of reversible obstructive airways disease which comprises administration to a patient suffering from such a condition of a therapeutically effective quantity of the compound of claim 1.

* * * * *